(12) United States Patent
Cottrell et al.

(10) Patent No.: US 7,345,092 B2
(45) Date of Patent: Mar. 18, 2008

(54) HIGH CONCENTRATION TOPICAL INSECTICIDES CONTAINING PYRETHROIDS

(75) Inventors: Ian W. Cottrell, Basking Ridge, NJ (US); Albert Ahn, Short Hills, NJ (US); Richard Fisher, Somerset, NJ (US); Christine M. Monro, East Hanover, NJ (US); Pierre R. Joseph, Hamilton, NJ (US)

(73) Assignee: Summit Vetpharm, LLC, Fort Lee, NJ (US)

( * ) Notice: Subject to any disclaimer, the term of this patent is extended or adjusted under 35 U.S.C. 154(b) by 548 days.

(21) Appl. No.: 10/910,542

(22) Filed: Aug. 3, 2004

(65) Prior Publication Data

US 2005/0009881 A1 Jan. 13, 2005

Related U.S. Application Data

(63) Continuation-in-part of application No. 10/242,551, filed on Sep. 12, 2002, now Pat. No. 6,867,223.

(60) Provisional application No. 60/493,976, filed on Aug. 8, 2003, provisional application No. 60/554,563, filed on Mar. 19, 2004.

(51) Int. Cl.
*A01N 43/08* (2006.01)
*A01N 43/40* (2006.01)
*A01N 53/08* (2006.01)
*A01N 57/10* (2006.01)
*A01N 37/00* (2006.01)
*A01N 37/02* (2006.01)
*A01N 37/06* (2006.01)

(52) U.S. Cl. ............... 514/471; 514/145; 514/345; 514/531; 514/549; 514/552; 514/875; 514/970

(58) Field of Classification Search ............... 514/345, 514/471, 531, 549, 552, 875, 970
See application file for complete search history.

(56) References Cited

U.S. PATENT DOCUMENTS

| | | | |
|---|---|---|---|
| 5,434,181 A | | 7/1995 | Kodaka et al. |
| 5,437,869 A | * | 8/1995 | Kelley ............... 424/406 |
| 5,532,365 A | | 7/1996 | Kodaka et al. |
| 6,096,329 A | | 8/2000 | Jeannin |
| 6,200,973 B1 | | 3/2001 | Sembo et al. |
| 6,201,017 B1 | * | 3/2001 | Sembo et al. ............... 514/471 |
| 6,274,570 B1 | | 8/2001 | Vogt et al. |
| 6,479,542 B2 | | 11/2002 | Sembo et al. |
| 6,566,392 B1 | | 5/2003 | Okada et al. |
| 6,588,374 B1 | | 7/2003 | Cottrell et al. |
| 6,663,876 B2 | | 12/2003 | Campbell et al. |
| 6,867,223 B2 | | 3/2005 | Cottrell et al. |
| 2003/0013684 A1 | | 1/2003 | Kawahara et al. |
| 2004/0050340 A1 | | 3/2004 | Cottrell et al. |
| 2004/0050341 A1 | | 3/2004 | Cottrell et al. |

FOREIGN PATENT DOCUMENTS

| | | | |
|---|---|---|---|
| EP | 0 979 606 A1 | | 2/2000 |
| EP | 976327 | * | 2/2000 |
| EP | 976328 | * | 2/2000 |
| JP | 3-220176 | | 9/1991 |
| WO | WO 02/05639 A2 | | 1/2002 |

OTHER PUBLICATIONS

CABA abstract 83:107933 (1994).*
CABA abstract 79:28333 (1994).*

* cited by examiner

*Primary Examiner*—John Pak
(74) *Attorney, Agent, or Firm*—Stroock & Stroock & Lavan LLP

(57) ABSTRACT

A topical insecticide preparation is provided which can be safe to use and avoids many common deleterious side effects of conventional topical insecticides. The topical insecticide contains a combination of a first pyrethroid insecticide effective for killing fleas, a second pyrethroid insecticide effective for killing ticks, and an insect growth regulator (IGR). The topical insecticide preparation can be packaged together or packaged so that the first and second pyrethroid insecticides are stored separately prior to administration of the insecticide preparation to the animal. The combination of the first and second pyrethroid insecticides with an insect growth regulator results in an insecticide preparation formulated to have enhanced insecticidal activity against fleas and ticks compared to the effectiveness of the first and second insecticides used alone. Further, the combination of the first and second pyrethroid insecticides with an insect growth regulator produces an insecticide preparation having enhanced insecticidal activity against fleas and ticks while advantageously minimizing the total amount of insecticide needed for its effectiveness.

17 Claims, No Drawings

HIGH CONCENTRATION TOPICAL INSECTICIDES CONTAINING PYRETHROIDS

This application claims the benefit of U.S. Provisional Application No. 60/493,976, filed Aug. 8, 2003, and U.S. Provisional Application No. 60/554,563, filed Mar. 19, 2004, and is a continuation-in-part of U.S. Ser. No. 10/242,551, filed Sep. 12, 2002 now U.S. Pat. No. 6,867,223, the contents of which are incorporated herein by reference.

BACKGROUND OF INVENTION

The invention relates generally to insecticides and more particularly to a topical insecticide, such as one suitable to use on house pets such as dogs.

The infestation of animals with fleas, ticks, flies and the like is highly undesirable. Accordingly, it has become common to administer both topical and internal insecticides to livestock and pets. Topical applications can be desirable, in that many insecticides are acceptably safe when used topically, but not when used internally. Also, many pet owners are concerned about administering internal insecticides to their pets.

Various topical insecticides have drawbacks. Some require a large volume to be applied to the animal. This can cause considerable mess and can lead to an unpleasant smell. Additionally, if the dosage of a topical insecticide is in a large volume, it can be easily shaken off by the animal, thereby reducing the effectiveness of the insecticide formulation. Also, when the animal is a house pet, there is a further complication in that the insecticide should be safe for human contact. It should also not lead to staining of furniture, carpeting and the like. Finally, even if safe, topical insecticides for house pets should not be irritating or lead to rashes, hair loss or exhibit other unpleasant side effects.

There is therefore a need for an improved topical insecticide that overcomes drawbacks of the prior art.

SUMMARY OF THE INVENTION

Generally speaking, in accordance with the invention, a topical insecticide, particularly one for use on pets, especially dogs, is provided. Formulations in accordance with the invention can be safe to use and can avoid many common deleterious side effects of conventional topical insecticides.

The invention provides a topical insecticide which contains a combination of insecticides and insect growth regulators which can be effective to kill fleas, flea eggs, flea larvae, ticks, tick eggs, tick larvae and tick nymphs. The selection of the combination of insecticides and insect growth regulators produces an insecticide having high insecticidal activity while allowing for a lower total amount of insecticide to be applied to the animal, compared to the effectiveness and amount required of the individual insecticides when used alone to achieve the same kill rate. The compositions derived herein can also be useful to improve the speed of result and decrease the reoccurrence, compared to other formulations.

The invention can provide an insecticidal composition which contains a combination of a first insecticide component in an insecticidally effective amount to achieve at least, e.g., an 80%, preferably 90% kill rate for fleas, a second insecticide component in an insecticidally effective amount to achieve at least, e.g. an 80%, preferably 90% kill rate for ticks, and a growth regulating effective amount of an insect growth regulator (IGR). In certain embodiments of the invention, the second insecticide is not a neo-nicotinoid, which is considered only effective against fleas. The combination of the two insecticide components and the insect growth regulator increases the effectiveness of the first and second insecticide compared to the effectiveness of the first and second insecticides when used alone and reduces the effective amount of the first and second insecticide compared to the effective amount of the first and second insecticide when used alone.

In one embodiment of the invention, at least one of the two insecticide components in the composition is a pyrethroid and in other preferred embodiments, the first and second insecticide components in the composition are pyrethroids. In a preferred embodiment of the invention, the first insecticide component in the composition comprises permethrin Alternative embodiments of the invention can include cyphenothrin or fenpropathrin. The second insecticide component comprises a (tetrahydro-3-furanyl)methylamine derivative of formula (1), identified below. Of course, it should be understood that the designations of which of the two is the first and which is the second is arbitrary and interchangeable. Also, the identification of an active ingredient, e.g., permethrin, is intended to also refer to other pharmaceutically active forms of the active ingredient, such as esters, salts, hydrochlorides, acid or base forms, isomers and so forth.

In another embodiment of the invention, the first insecticide component comprises permethrin or phenothrin. The second insecticide component comprises a chloronicotinyl insecticide, preferably acetamiprid. Other chloronicotinyl insecticides that can be utilized in the insecticide formulation include, but are not limited to nitenpyram and imidacloprid, thiamethoxam, and clothianidin.

In another preferred embodiment of the invention, the first insecticide component comprises permethrin or phenothrin, and the second insecticide component comprises dinotefuran, acetamiprid, nitenpyram, imidacloprid, or bifenthrin. The second component is advantageously in combination with an isoparaffinic solvent such as Isopar®, available commercially from EXXON and/or tripropylene glycol methyl ether (TPM), dipropylene glycol methyl ether, propylene glycol methyl ether, ethyl lactate, propylene carbonate and/or safflower oil. It should be noted that in embodiments where the second insecticide is dinotefuran, Isopar and safflower oil are preferably not included in the solvent solution.

It has been determined that it is difficult to form a high concentration of dinotefuran and permethrin or phenothrin and it is likely to result in a solution that can be unstable when stored at room temperature for reasonable amounts of time. Accordingly, it was determined to be preferable to package the insecticide composition in a manner so that the first insecticide and second insecticide are not permitted to interact prior to application of the insecticide composition to the animal and to keep these formulations separated until application. The first and second insecticides can be stored separately from each other in a package or container having two associated, preferably attached, but individual chambers to prevent the mixing of the insecticides prior to the administration of the formulation. Prior to administration, the packages containing the two insecticides in their respective separate chambers are opened, and the two insecticides are dispensed simultaneously or at least at about the same time, to the animal.

In yet another preferred embodiment of the invention, the insect growth regulator in the composition is pyriproxyfen or methoprene. Preferably, the insect growth regulator is packaged in the same chamber as either the first insecticide or the second insecticide or in yet another container. Pyriproxyfen or methoprene are insecticides that act as an insect growth inhibitor (IGR) by preventing flea eggs from hatching.

In another preferred embodiment of the invention, triphenyl phosphate (TPP) is added to the insecticide composition, preferably in an amount less than the insecticidally effective amount of the first and second insecticide in the composition. Triphenyl phosphate can be packaged in the same container as either the first insecticide or the second insecticide. The selection of the chamber depends on the solvent in which the insecticide is solubilized.

Accordingly, it is an object of the invention to provide an improved topical insecticide composition that is highly effective against fleas, flea larvae, flea eggs, and ticks.

Another object of the invention is the provision of methods for controlling insect infestation.

Another object of the invention is to provide a topical insecticide that works more rapidly and/or more permanently than other insecticides.

Other objects and features will be in part apparent and in part pointed out.

DETAILED DESCRIPTION OF THE PREFERRED EMBODIMENTS

In accordance with the invention, insecticidal compositions, which contain a combination of insecticides and insect growth regulators effective to kill fleas and ticks, including flea eggs, flea larvae, and adult fleas and ticks, tick eggs, tick larvae and tick nymphs, are provided. By selecting a combination of insecticides that are highly effective against fleas and combining them with insecticides that are highly effective against ticks, the total amount of insecticide is optimized. The combination of insecticides and insect growth regulators result in insecticidal compositions having high insecticidal activity against fleas and ticks while allowing for a reduced amount of the total volume of insecticide required for application when compared to compositions containing the individual insecticides alone. Compositions containing permethrin in accordance with the invention are particularly advantageous for use on dogs, compared to their use on cats.

The insecticidal compositions in accordance with the invention comprise a combination of a first insecticide component in an insecticidally effective amount to preferably achieve at least an 80% kill rate for fleas, a second insecticide component in an insecticidally effective amount to preferably achieve at least an 80% kill rate for ticks, and an insecticidally effective amount of an insect growth regulator (IGR). The combination of the first and second insecticide components with an insect growth regulator advantageously results in an insecticidal composition having a higher insecticidal activity against fleas, flea larvae, flea eggs and ticks compared to a composition containing either the first or second insecticide or the insect growth regulator alone.

In a preferred embodiment of the invention, the first insecticide component in the composition is in an insecticidally effective amount to achieve at least an 80% kill rate for fleas, more preferably at least a 90% kill rate for fleas, even more preferably at least a 95% kill rate for fleas, and most preferably, at least a 99% kill rate for fleas. In another preferred embodiment of the invention, the second insecticide component in the composition is in an insecticidally effective amount to achieve at least an 80% kill rate for ticks, more preferably at least a 90% kill rate for ticks, even more preferably, at least a 95% kill rate for ticks, and most preferably, at least a 99% kill rate for ticks.

In one embodiment of the invention, the first and second insecticide components in the composition are not the same insecticide and at least one of the two insecticides in the composition is a pyrethrin or a synthetic pyrethroid. In other preferred embodiments of the invention, the first and second insecticide components in the composition are both pyrethroids. It should of course be understood that additional pyrethroids or non-pyrethroid insecticides can also be included.

In another embodiment of the invention, the first insecticide component is a pyrethroid, and the second insecticide component is a neo-nicotinoid.

In one preferred embodiment of the invention, the first insecticide component in the composition comprises a pyrethroid, preferably permethrin. Other embodiments of the invention include cyphenothrin and/or fenpropathrin as the first insecticide component. The second insecticide component preferably comprises a neo-nicotinoid comprising a (tetrahydro-3-furanyl)methylamine derivative of following formula (1). The (tetrahydro-3-furanyl)methylamine derivatives of the formula (1) have an excellent insecticidal activity even in the absence of a pyridylmethyl group or a thiazolylmethyl group in their molecular structure.

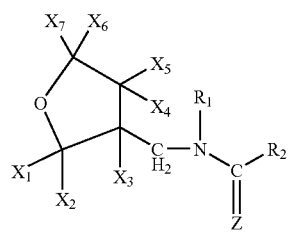

(1)

where $X_1$, $X_2$, $X_3$, $X_4$, $X_5$, $X_6$ and $X_7$ each represent each a hydrogen atom or an alkyl group having from 1 to 4 carbon atoms; $R_1$ represents a hydrogen atom, an alkyl group having from 1 to 5 carbon atoms, an alkenyl group having 3 carbon atoms, a benzyl group, an alkoxyalkyl group having from 2 to 4 carbon atoms (in its whole group), an alkyloxycarbonyl group having from 1 to 3 carbon atoms, a phenoxy carbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group or an N,N-dimethylcarbamoyl group; $R_2$ represents a hydrogen atom, an amino group, a methyl group, an alkylamino group having from 1 to 5 carbon atoms, a di-substituted alkylamino group having from 2 to 5 carbon atoms (in its whole group), a 1-pyrrolidinyl group, an alkenylamino group having 3 carbon atoms, an alkynylamino group having 3 carbon atoms, a methoxyamino group, an alkoxyalkylamino group having from 2 to 4 carbon atoms (in its whole group), a methylthio group or $-N(Y_1)Y_1$ (where $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group, an N,N-dimethylcarbamoyl group, a (tetrahydro-3-furanyl) methyl group or a benzyl group, and $Y_2$ represents a hydrogen atom or an alkyl group having from 1 to 5 carbon atoms); and Z represents =N—$NO_2$, =CH—$NO_2$ or =N—CN.

Intermediates for producing the compounds of the formula (1) are represented by a formula (2):

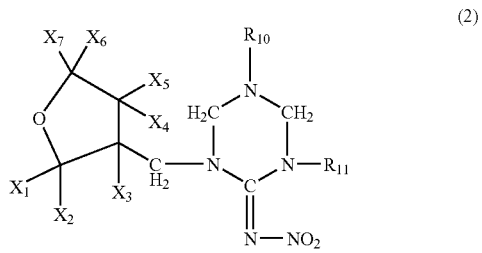

(2)

where $X_1$, $X_2$, $X_3$, $X_4$, $X_5$, $X_6$ and $X_7$ each represent each a hydrogen atom or an alkyl group having from 1 to 4 carbon atoms; $R_{10}$ represents an alkyl group having from 1 to 5 carbon atoms or a benzyl group; and R11 represents an alkyl group having from 1 to 5 carbon atoms or a benzyl group.

The (tetrahydro-3-furanyl)methylamine derivatives of the formula (1) and formula (2) according to the invention are excellent compounds having a high insecticidal activity and broad insecticidal spectrum. Further, agricultural chemicals containing the (tetrahydro-3-furanyl)methylamine derivatives of formula (1) and (2) according to the invention have outstanding characteristics as insecticides and hence are useful.

Specific examples of the alkyl group for $X_1$, $X_2$, $X_3$, $X_4$, $X_5$, $X_6$ and $X_7$ in the above formulae (1) and (2) include a methyl group, an ethyl group, an n-propyl group, an iso-propyl group, a tert-butyl group, and the like, preferably a methyl group.

Specific examples of the alkyl group for $R_1$ include a methyl group, an ethyl group, an n-propyl group, an iso-propyl group, an n-butyl group, an iso-butyl group, a sec-butyl group, a tert-butyl group, an n-pentyl group, and the like.

Specific examples of the alkenyl group for $R_1$ include a 1-propenyl group, a 2-propenyl group, and the like.

Specific examples of the alkoxyalkyl group for $R_1$ include a methoxymethyl group, an ethoxymethyl group, an n-propoxymethyl group, an iso-propoxymethyl group, a methoxyethyl group, an ethoxyethyl group, and the like.

Specific examples of the alkyloxycarbonyl group for $R_1$ include a methyloxycarbonyl group, an ethyloxycarbonyl group, an n-propyloxycarbonyl group, an iso-propyloxycarbonyl group, and the like.

Specific examples of the alkylcarbonyl group for $R_1$ include a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group, a tert-butylcarbonyl group, an n-pentylcarbonyl group, an n-hexylcarbonyl group, and the like.

Specific examples of the alkenylcarbonyl group for $R_1$ include a vinylcarbonyl group, a 1-methylvinylcarbonyl group, and the like.

Specific examples of the cycloalkylcarbonyl group for $R_1$ include a cyclopropylcarbonyl group, a cyclobutylcarbonyl group, a cyclopentylcarbonyl group, a cyclohexylcarbonyl group, and the like.

Specific examples of the benzoyl group substituted by alkyl group(s) for $R_1$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) for $R_1$ include a 2-chlorobenzoyl group, a 3-chlorobenzoyl group, a 4-chlorobenzoyl group, a 3,4-dichloro-benzoyl group, a 4-fluorobenzoyl group, and the like.

Although $R_1$ can take various substituents as described above, it is preferably a hydrogen atom, an alkylcarbonyl group having from 1 to 4 carbon atoms or a cyclopropylcarbonyl group.

Specific examples of the alkylamino group for $R_2$ include a methylamino group, an ethylamino group, an n-propylamino group, an iso-propylamino group, an n-butylamino group, an iso-butylamino group, a sec-butylamino group, a tert-butylamino group, an n-pentylamino group, and the like, preferably a methylamino group.

Specific examples of the di-substituted alkylamino group for $R_2$ include a dimethylamino group, a diethylamino group, an N-methyl-N-ethylamino group, an N-methyl-N-n-propylamino group, an N-methyl-N-n-butylamino group, and the like, preferably a dimethylamino group.

Specific examples of the alkenylamino group for $R_2$ include a 1-propenylamino group, a 2-propenylamino group, and the like.

Specific examples of the alkynylamino group for $R_2$ include a propargylamino group, and the like.

Specific examples of the alkoxyalkylamino group for $R_2$ include a methoxymethylamino group, an ethoxymethylamino group, an n-propoxymethylamino group, an iso-propoxymethylamino group, a methoxyethylamino group, an ethoxyethylamino group, and the like.

Specific examples of the alkyloxycarbonyl group denoted by $Y_1$ for $R_2$ include a methyloxycarbonyl group, an ethyloxy-carbonyl group, an n-propyloxycarbonyl group, an iso-propyloxy-carbonyl group, and the like.

Specific examples of the alkylcarbonyl group denoted by $Y_1$ for $R_2$ include a methylcarbonyl group, an ethylcarbonyl group, an n-propylcarbonyl group, an iso-propylcarbonyl group, an n-butylcarbonyl group, an isobutylcarbonyl group, a sec-butylcarbonyl group, a tertbutylcarbonyl group, an n-pentylcarbonyl group, an n-hexylcarbonyl group, and the like, preferably a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group and a tert-butylcarbonyl group.

Specific examples of the alkenylcarbonyl group denoted by $Y_1$ for $R_2$ include a vinylcarbonyl group, a 1-methylvinylcarbonyl group, and the like.

Specific examples of the cycloalkylcarbonyl group denoted by $Y_1$ for $R_2$ include a cyclopropylcarbonyl group, a cyclobutylcarbonyl group, a cyclopentylcarbonyl group, a cyclohexylcarbonyl group, and the like, preferably a cyclopropyl-carbonyl group.

Specific examples of the benzoyl group substituted by alkyl group(s) denoted by $Y_1$ for $R_2$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) denoted by $Y_1$ for $R_2$ include a 2-chlorobenzoyl group, a 3-chlorobenzoyl group, a 4-chlorobenzoyl group, a 3,4-dichlorobenzoyl group, a 4-fluoro benzoyl group, and the like.

Specific examples of the alkyl group denoted by $Y_1$ for $R_2$ include a methyl group, an ethyl group, an n-propyl group, an iso-propyl group, an n-butyl group, an iso-butyl group, a sec-butyl group, a tert-butyl group, an n-pentyl group, and the like, preferably a methyl group.

In the formula (1), compounds in which $R_1$ and $Y_1$ are concurrently an alkylcarbonyl group having from 1 to 4 carbon atoms or a cyclopropylcarbonyl group are preferred from the viewpoint of both insecticidal activity and production method.

It has been determined that the combination of two different insecticides and an insect growth regulator results in a composition having high insecticidal activity when compared to compositions containing the first or second insecticide alone. Minimizing the amount of total insecticide administered to an animal is advantageous in order to reduce concerns regarding toxicity of the insecticide to the animal, thereby providing for safer use. It is also useful to decrease transfer of the insecticide onto humans, clothing and furniture. Therefore, the present invention allows for a lower amount of insecticide to be administered to control insect infestation than would otherwise be possible using the single insecticides alone.

In a preferred embodiment of the invention, the first insecticide component in the composition comprises a pyrethroid and the second insecticide component comprises a neo-nicotinoid. In a preferred embodiment of the invention, the first insecticide component comprises cyclopropanecarboxylic acid, 3-(2,2-dichlorethenyl)-2,2-dimethyl-, (3-phenoxyphenyl)methyl ester (permethrin), and the second insecticide component comprises 1-{(tetrahydro-3-furanyl) methyl}-2-nitro-3-methylguanidine (dinotefuran) or N-((6-chloro-3-pyridinyl)methyl)-$N^1$-cyano-N-methyl-ethanimidanide (acetamiprid). Permethrin is an acaricide that will kill ticks, and dinotefuran and acetamiprid are insecticides that will kill adult fleas. In a preferred embodiment of the invention, the composition further contains an insect growth regulator, which is preferably pyriproxyfen or methoprene.

In another preferred embodiment of the invention, the first insecticide component in the composition comprises 2,2-Dimethyl-3-(2-methyl-1-propenyl)cyclopropanecarboxylic acid, (3-phenoxyphenyl)methyl ester (phenothrin), and the second insecticide component comprises dinotefuran or acetamiprid.

Dinotefuran can be dissolved in particularly effective solvent systems such as a combination of water and ethanol or isopropanol, as disclosed in pending U.S. Ser. No. 10/242,552, filed Sep. 12, 2002, which is now U.S. Pat. No. 6,867,223, incorporated by reference, or in phenyl methanol or ethanol, as disclosed in U.S. Pat. No. 6,588,374, incorporated by reference, or in ethyl lactate and water combinations. In a preferred embodiment of the invention, the composition further contains an insect growth regulator, which is preferably pyriproxyfen or methoprene.

The insecticide compositions of the invention contain a combination of insecticides and insect growth regulators which are effective to kill fleas, flea eggs, flea larvae, ticks, tick eggs, tick larvae and tick nymphs. The selection of the first insecticide component, the second insecticide component and insect growth regulator produces an insecticide having high insecticidal acitivity. In a preferred embodiment of the invention, the first insecticide component or the second insecticide component is an acaricide, and even more preferred, the first insecticide component or the second insecticide component is permethrin.

Of course, it should be understood that the insecticide composition may contain one or more acaricides or other physiologically active ingredients. Additional acaricides that may be utilized in the insecticide composition include but are not limited to, the following class of compounds: antibiotic acaricides (nikkomycins, thuringiensin); macrocyclic lactone acaricides (tetranactin); avermectin acaricides (abamectin, doramectin, eprinomectin, ivermectin, selamectin); milbemycin acaricides (milbemectin, milbemycin oxime, moxidectin); bridged diphenyl acaricides (azobenzene, benzoximate, benzyl benzoate, bromopropylate, chlorbenside, chlorfenethol, chlorfenson, chlorfensulphide, chlorobenzilate, chloropropylate, DDT, dicofol, diphenyl sulfone, dofenapyn, fenson, fentrifanil, fluorbenside, proclonol, tetradifon, tetrasul); carbamate acaricides (benomyl carbanolate, carbaryl, carbofuran, methiocarb, metolcarb, promacyl, propoxur); oxime carbamate acaricides (aldicarb, butocarboxim, oxamyl, thiocarboxime, thiofanox); dinitrophenol acaricides (binapacryl, dinex, dinobuton, dinocap, dinocap-4, dinocap-6, dinocton, dinopenton, dinosulfon, dinoterbon, DNOC); formamidine acaricides (amitraz chlordimeform, chloromebuform, formetanate, formparanate); mite growth regulators (clofentezine, dofenapyn, fluazuron, flubenzimine, flucycloxuron, flufenoxuron, hexythiazox); organochlorine acaricides (bromocyclen, camphechlor, DDT, dienochlor, endosulfan, lindane); organophosphorus acaricides (chlorfenvinphos, crotoxyphos, dichlorvos, heptenophos, mevinphos, monocrotophos, naled, schradan, TEPP, tetrachlorvinphos); organothiophosphate acaricides (amidithion, amiton, azinphos-ethyl, azinphos-methyl, azothoate, benoxafos, bromophos, bromophos-ethyl, carbophenothion, chlorpyrifos, chlorthiophos, coumaphos, cyanthoate, demeton, demeton-O, demeton-S, demeton-methyl, demeton-O-methyl, demeton-S-methyl, demeton-S-methylsulphon, dialifos, diazinon, dimethoate, dioxathion, disulfoton, endothion, ethion, ethoate-methyl, formothion, malathion, mecarbam, methacrifos, omethoate, oxydeprofos, oxydisulfoton, parathion, phenkapton, phorate, phosalone, phosmet, phoxim, pirimiphos-methyl, prothidathion, prothoate, pyrimitate, quinalphos, quintiofos, sophamide, sulfotep, thiometon, triazophos, trifenofos, vamidothion); phosphonate acaricides (trichlorfon); phosphoramidothioate acaricides (isocarbophos, methamidophos, propetamphos); phosphorodiamide acaricides (dimefox, mipafox); organotin acaricides (azocyclotin, cyhexatin, fenbutatin oxide); phenylsulfamide acaricides (dichlofluanid); phthalimide acaricides (dialifos, phosmet); pyrazole acaricides (acetoprole, fipronil, tebufenpyrad, vaniliprole); pyrethroid acaricides such as pyrethroid ester acaricides (acrinathrin, bifenthrin, cyhalothrin, cypermethrin, alpha-cypermethrin, fenpropathrin, fenvalerate, flucythrinate, flumethrin, fluvalinate, tau-fluvalinate, permethrin) and pyrethroid ether acaricides (halfenprox); pyrimidinamine acaricides (pyrimidifen); pyrrole acaricides (chlorfenapyr); quinoxaline acaricides (chinomethionat, thioquinox); sulfite ester acaricides (propargite); tetronic acid acaricides (spirodiclofen); thiocarbamate acaricides (fenothiocarb); thiourea acaricides (chloromethiuron, diafenthiuron); and other unclassified acaricides (acequinocyl, amidoflumet, arsenous oxide, bifenazate, closantel, crotamiton, disulfiram, etoxazole, fenazaflor, fenazaquin, fenpyroximate, fluacrypyrim, fluenetil, mesulfen, MNAF, nifluridide, pyridaben, sulfiram, sulfluramid, sulfur, triarathene).

Other acaricides or other physiologically active substances that may be utilized in the insecticide composition of the present invention are acephate, *Bacillus thuringiensis aizawai*, *Bacillus thuringiensis kurstaki*, *Beauveria bassiana*, Bendiocarb, Bifenthrin, Carbaryl, Chlopyrifos+DDVP, Chlorpyrifos+pyrethrin, Cyfluthrin, Ethoprop, Fenamiphos, Fenoxycarb, Fipronil, Fonofos, Halofenozide, Heterorhabditis bacteriophora, Hydramethylnon, Imidacloprid, Isofenphos, Lambda-cyhalothrin, Lindane, Malathion, Myrothecium verrucaria, Permethrin, Spinosad, and Trichlorfon, Acequinocyl, Acetamiprid, Acibenzolar-S-Methyl, Azoxystrobin, Boscalid, Bromuconazole, Carfentrazone-ethyl, Clodinafop-Propargyl, Clofencet, Cloransulam-methyl, Clothianidin, Copper Octanoate, Cuprous Chloride, Cyclanilide, Cyhalofop-butyl, Cymoxanil, Cyprodinil, Diclosulam, Diflufenzopyr, Dimethomorph, Ecolyst, Etoxazole, Fenhexamid, Fluazinam, Flufenacet, Flumioxazin, Fluroxypyr, Fluthiacet-Methyl, Famoxadone, Foramsulfuron, Imazamox, Imiprothrin, Indoxacarb, Isoxaflutole, Kresoxim-methyl, Lithium Perfluorooctane Sulfonate (LPOS), Mesotrione, N-Methylneodecanamide, Novaluron, Phosphine, Pirimicarb, Prohexadione Calcium, Propazine, Pymetrozine, Spinosad, Sulfentrazone, Tebufenpyrad, Thiacloprid, Thiazopyr, Tolylfluanid, Tralkoxydim, Trifloxystrobin, Zoxamide, Amitraz, chrorpyrifos, chrorpyrifos plus cypermethrin, chrorpyrifos plus dizinon, chrorpyrifos plus permethrin, coumaphos, crotozyphos plus dichlorvos, cyfluthrin, cypermethrin, diazinon, dichlorvos, dichlorvos plus pyrethrins, dichlorvos plus tetrachlorvinphos, dimethoate, doramectin, eprinomectin, ethion, famphur, fenthion, fenvalerate, ivermectin, lambda-cyhalothrin, lambda-cyhalothrin plus pirimiphos methyl, lindane, malathion, malathion plus methoxychlor, malathion plus sulphur, methomyl, methoxychlor, methoxychlor plus pyrethrins, moxidectin, naled, nithiazine, permethrin plus pyrethrins, phosmet, pirimiphos methyl, and pyrethrins.

It has been determined that it is difficult to form a high concentration of dinotefuran and permethrin or phenothrin and it is likely to result in a solution that can be unstable when stored at room temperature for reasonable amounts of time. Accordingly, it is preferable that these two insecticides are packaged in a container having two associated, preferably attached, but individual chambers to prevent the mixing of the insecticides prior to the administration of the formulation. Prior to administration, the container can be opened and the two insecticides can be dispensed simultaneously or nearly simultaneously, to the companion animal.

In another embodiment of the invention, one of the active ingredients, for e.g., dinotefuran or permethrin, can be encapsulated or contained in micelles in the formulation. In this embodiment of the invention, topical formulations can be packaged and stored in a single container prior to administration to the animal.

In a preferred embodiment of the invention, the insecticide composition of the invention is packaged in a single dose package. Single dose containers make storage and disposal more convenient for animal owners. Preferably, the insecticide composition is packaged in a container encompassing two associated, preferably attached but individual chambers, which are separated by a barrier, preferably plastic, plastic coated paper or metal, such as aluminum foil. In one embodiment of the invention, the first chamber and the second chamber are plastic tubes that are separate but fused together. During packaging, the first insecticide, preferably permethrin or phenothrin, is placed in the first chamber and the second insecticide, preferably dinotefuran or acetamiprid, is placed in the second chamber. Preferably, the first and second chambers are separated by a barrier that prevents the interreaction of the first and second insecticides. In another preferred embodiment of the invention, an insect growth regulator, preferably methoprene or pyriproxfen, is added to the insecticide composition and placed in the same chamber with either the first insecticide or the second insecticide or even separately in yet another container.

The entire container containing the two insecticides in separate chambers is sealed, preferably with a tab or top, for use in opening the container prior to administration. After the container is sealed, the insecticide formulation can be safely stored in the container until administration of the insecticide formulation to the animal.

Prior to administration of the insecticide formulation to the animal, the container is opened by removing the tab or top. In one embodiment of the invention, the container is opened by twisting the tab thereby resulting in breaking or tearing of the barrier separating the two chambers, thereby allowing the two insecticides, preferably permethrin and dinotefuran, to mix prior to administration of the insecticide formulation to the animal. After the two insecticides are mixed, the two insecticides are dispensed simultaneously by squeezing or collapsing the body of the container. A dual plunger system can also be employed to administer the formulation to the animal.

It is of course understood that the two insecticides need not be mixed together prior to administration of the insecticide formulation to the animal. Accordingly, in another embodiment of the invention, opening of the dual-chamber container does not result in the mixing of the two insecticides. After the container is opened, the two insecticides are dispensed onto the animal by squeezing or collapsing the container or containers, either simultaneously or sequentially.

In one embodiment of the invention, the composition is packaged with instructions, advising to mix the insecticides. In other embodiments of the invention, the instructions will direct the user to mix the insecticides upon application.

Because compositions in accordance with preferred embodiments of the invention have a high concentration of insecticide, a relatively small application of a spot or line on the animal can effectively prevent and control flea and tick infestation on the animal for up to four weeks post-administration. Preferably, the insecticide formulation is non-toxic and does not irritate the animal's skin. Applications are typically in the range of 0.5 to 10 ml. In certain embodiments of the invention, the compositions are applied in the range of about 0.05 to 0.5 ml/kg of animal body weight.

In one preferred embodiment of the invention, the insecticide composition comprises permethrin in a concentration range of between 40 to 65%, dinotefuran in a concentration range of 5 to 15%, and pyriproxyfen or methoprene in a concentration range of 1 to 3%. All percentages, unless otherwise specified, are on a weight basis. While an effective dosage of the insecticide composition needs to be applied to the animal for optimum effectiveness against fleas, flea eggs, flea larvae and ticks, the active dosages of the first insecticide and second insecticide depend upon the size of the animal. Compositions containing permethrin are particularly advantageous for use on dogs, compared to their use on cats.

Preferably, up to 4 ml of insecticide may be administered to a dog weighing 89-140 pounds. Such composition will preferably contain at least about 1300 to 2600 mg permethrin, at least about 300 mg dinotefuran, and at least about 20 mg of pyriproxfen.

Preferably, up to 3 ml of insecticide may be administered to a dog weighing 45 to 88 pounds. Such composition will preferably contain at least about 910 to 1800 mg permethrin, at least about 240 mg dinotefuran, and at least about 16 mg of pyriproxfen.

Preferably, up to 2.1 ml of insecticide may be administered to a dog weighing 23 to 44 pounds. Such composition will preferably contain at least about 455 to 1300 mg permethrin, at least about 210 mg dinotefuran, and at least about 14 mg of pyriproxfen.

Preferably, up to 1.5 ml of insecticide may be administered to a dog weighing 22 pounds or less. Such composition will preferably contain at least about 175 to 650 mg permethrin, at least about 150 mg dinotefuran, and at least about 10 mg of pyriproxfen.

In another preferred embodiment of the invention, the insecticide composition comprises phenothrin, dinotefuran and pyriproxfen. Insecticide compositions containing phenothrin in accordance with the invention are particularly advantageous for use on both dogs and cats. Preferably, the insecticide composition comprises phenothrin in a concentration range of between 80 to 87%, more preferably approximately 85.7%, dinotefuran in a concentration range of 5 to 15%, and pyriproxyfen or methoprene in a concentration range of 1 to 2%. All percentages, unless other specified, are on a weight basis. The actual amount of the active dosage of phenothrin will vary depending on the size of the dog or cat.

It should be noted that in embodiments where the formulation is packaged using separate chambers or containers, the precentage of an active ingredient provided is the percentage of that active ingredient in a single solution. For example, 1 to 2% pyriproxyfen is the concentration of pyriproxfen contained in the formulation in a single chamber rather than the concentration of pyriproxyfen in the total formulation of the combined chambers.

For use on cats, up to 1.1 ml of total insecticide may preferably be administered to a cat weighing less than 10 pounds and up to 1.5 ml of insecticide may be administered to a cat weighing 10 pounds or more. Preferably, the volume of phenothrin being administered to a cat is between about 0.25 to 0.85 ml for a cat weighing less than 10 pounds and between about 0.35 and 1.25 ml for a cat weighing 10 pounds or more. A volume of 1.0 ml and 1.3 ml, respectively, for a phenothrin containing product is preferred.

Insecticide compositions containing phenothrin are also particularly effective for use on dogs. Preferably, approximately up to 1.5 ml of total insecticide may be administered to a dog weighing under 30 pounds, approximately up to 3.0 ml of total insecticide may be administered to a dog weighing less than 45 pounds, approximately up to 4.1 ml of total insecticide may be administered to a dog weighing 41-60 pounds, approximately up to 4.6 ml of total insecticide may be administered to a dog weighing 61-90 pounds, and approximately up to 6.0 ml of total insecticide may be administered to a dog weighing over 90 pounds. Preferably, the amount of phenothrin in the insecticide composition is between 0.3 to 0.9 ml for a dog weighing 4 to 15 pounds, between about 0.25 to 0.85 ml for a dog weighing 16 to 30 pounds, between about 0.65 to 1.95 ml for a dog weighing 31 to 45 pounds, between about 1.0 to 3.0 ml for a dog weighing 46 to 60 pounds, between about 1.15 to 3.45 ml for a dog weighing 61 to 90 pounds, and between about 1.5 to 4.5 ml for a dog weighing more than 90 pounds.

In another preferred embodiment of the invention, the insecticide composition comprises permethrin, acetamiprid and pyriproxyfen. Preferably, the insecticide composition comprises permethrin in a concentration range of 45 to 65%, acetamiprid in a concentration range of 5 to 50%, and pryriproxfen in a concentration range of 0.5 to 5%.

In another preferred embodiment of the invention, the insecticide composition comprises phenothrin, acetamiprid and pyriproxyfen. Preferably, the insecticide composition comprises phenothrin in a concentration range of 5 to 90%, acetamiprid in a concentration range of 5 to 50%, and pryriproxfen in a concentration range of 0.5 to 5%.

Preferably, the insecticidal compositions of the present invention further comprises an enzyme inhibitor or a synergist such as piperonyl butoxide, N-octylbicycloheptenedicarboximide, triphenyl phosphate, which preferably increases the efficacy of the composition. Preferably, the insecticidal compositions also contain one or more compounds to increase the efficacy and to reduce the irritation of pyrethroid insecticides to the skin of animals.

In a preferred embodiment, the insecticidal compositions further comprise an effective amount of triphenyl phosphate (TPP) to increase efficacy, typically less than the amount of active ingredient. The amount of TPP to include in the composition relative to the concentration of the first and second insecticide component in the composition can be readily determined using routine experimentation to determine the optimum synergistic effect.

In the preparation of a formulation for use on animals, there are several parameters that should be considered. These are:

(a) Concentration high enough to minimize the volume of the topical applied to the animal (one would not want to put 20 ml, e.g., onto a small dog).

(b) Concentration low enough to achieve effective translocation of the topical insecticide over the animal's skin.

(c) The formulation should be stable for one month at 130° F., 110° F., 40° F., room temperature and 0° F. This helps ensure that the formulation remains stable under the conditions that it could meet in commerce.

(d) Safe to use on the intended animal—particularly non-irritating to at least the intended animal, since the product is applied to the skin. Also safe if ingested by the animal; ingestion can occur when pets groom themselves.

(e) Safe to use by the consumer.

(f) Efficacious in use—should kill greater than 90% of the fleas and ticks up to 28 days.

(g) Efficacy would be reduced if crystallization occurred in the package.

(h) Needs to be aesthetically pleasing—"no oily drop" on the animal when applied.

(i) Fast drying to reduce the chance of the animal shaking off the liquid thereby reducing efficacy.

j) Microbiologically stable.

Other additives to the insecticidal composition include but are not limited to fragrances, surfactants and spreading agents to increase performance such as polysorbate 20 and polysorbate 80, and isopropyl myristate. Polymers such as agar, gelatin, alginate, and cationic polymers such as cationic agar, cationic cellulose, cationic acrylates, and polyoxymethylene urea may also be added to provide enrobing of the insecticide to improve safety and adhesion to skin and hair.

In practice, an effective amount of the insecticidal compositions as described herein may be applied to a companion animal, preferably a dog, as a foaming shampoo, dip, aerosol spray, pump spray, powder, lotion, emulsifiable concentrate, aqueous or liquid flowable, suspension concentrate and by any other methods suitable for administering topical compositions to animals.

The preparations are suitable for combating insect infestations which occur in animal husbandry and animal breeding in productive, breeding, zoo, laboratory, experimental animals and pets, and have a favorable toxicity to warm-blooded animals. Productive and breeding animals include mammals, such as, for example, cattle, horses, sheep, pigs, goats, camels, water buffalo, donkeys, rabbits, fallow deer and reindeer, and pelt animals, such as, for example, mink, chinchilla and raccoons.

Laboratory and experimental animals include mice, rats, guinea pigs, hamsters, dogs and cats.

Pets include dogs and cats and many of the laboratory and experimental animals.

The formulation according to the invention is particularly preferably administered to companion animals such as dogs and cats, but can be suitable for other mammals.

The following examples are given for purposes of illustration only and are not intended to be construed in a limiting manner.

EXAMPLES

Example 1

Preparation of 1-{(tetrahydro-3-furanyl)methyl}-2-nitro-3-methylguanidine (dinotefuran)

A mixture comprising 10.0 g of (tetrahydro-3-furanyl) methanol, 29.5 g of trifluoromethanesulfonic anhydride, 10.0 g of pyridine and 200 ml of dichloromethane was stirred for an hour at room temperature. Water was poured into the reaction solution to separate the organic layer, which was washed with 1 N hydrochloric acid, water and a saturated saline solution, dried, and concentrated to obtain 20 g of 3-tetrahydro-furanylmethyl triflate. 3.25 g of 60% sodium hydride were added to 12.5 g of 1,5-dimethyl-2-nitroiminohexahydro-1,3,5-triazine and 60 ml of DMF at room temperature, followed by stirring for an hour. 20.0 g of the 3-tetrahydrofuranylmethyl triflate were added thereto, and the mixture was stirred at 50° C. for 2 hours. After cooling the mixture to room temperature, 50 ml of 2N hydrochloric acid were added thereto, followed by stirring at 50° C. for 2 hours. The resultant mixture was neutralized with sodium bicarbonate and extracted with dichloromethane, and the extract was dried and concentrated. The residue thus obtained was purified by silica gel column chromatography (eluent: 1:1 ratio of ethyl acetate/hexane) to obtain 7.8 g of 1-{(tetrahydro-3-furanyl)methyl}-2-nitro-3-methylguanidine (dinotefuran).

Example 2

Preparation of Insecticide Formulation Containing Dinotefuran and Pyriproxyfen 25 g of dinotefuran was added to 100 ml phenyl methanol with stirring until it dissolved. 1 g of pyriproxyfen was added to the solution with stirring to produce a clear, homogeneous solution of high insecticide concentration.

The resulting solution can be spot applied to companion animals, such as dogs and will kill fleas, ticks and other insects.

Example 3

Preparation of Insecticide Formulation Containing Permethrin, Dinotefuran and Pyriproxyfen Permethrin (65 g) was added to a clean container. Safflower oil (35 g) was added with stirring until the solution was homogeneous. This solution containing permethrin and safflower oil was added to one of the chambers in the package in the appropriate volume based on the dosage required.

Pyriproxyfen (1 g) and Mackernium KP (1 g) were added to a clean container, and gently heated until the pyriproxyfen liquefied. Water (27.6 g) was added with stirring, followed by the addition of ethyl lactate (55.4 g). Dinotefuran (15 g) was added and the solution was mixed and heated at 50° C. until the dinotefuran dissolved. The solution was cooled to room temperature and the pH adjusted to 5.5 by the addition of sodium carbonate (0.15 g of a 25% aqueous solution). This solution was added to the other chamber in the package in the appropriate volume based on the dosage required.

Example 4

Stability of Permethrin/Dinotefuran/Pyriproxfen Formulation

Compositions containing dinotefuran and pyriproxyfen prepared according to the methodology of Example 3 are stable for at least 1 month at 130° F., 3 months at 110° F., 1 month at 40° F. and 1 month at room temp. (approx. 70° F.). The stability of the formulation is based on the criterion of no crystal formation during a 1 month period.

Example 5

Preparation of Insecticide Formulation Containing Permethrin, Acetamiprid and Pyriproxfen 10 grams acetamiprid was added to 89 grams ethanol and stirred until the acetamiprid dissolved. 1 gram of pyriproxyfen was added to this solution and stirred until it dissolved. This solution was added to the appropriate chamber in the dual chamber package.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following embodiments are intended to cover all of the generic and specific features of the invention herein described and all statements of the scope of the invention which, as a matter of language, might be said to fall therebetween.

Particularly it is to be understood that in said embodiments, ingredients or compounds recited in the singular are intended to include compatible mixtures of such ingredients wherever the sense permits.

What is claimed is:

1. An insecticidal preparation, comprising a first insecticide composition comprising permethrin in an insecticidally effective amount to kill fleas, a second insecticide composition comprising dinotefuran in an insecticidally effective amount to kill ticks, the first composition packaged in a manner in which it is separated from the second composition, in order to prevent interaction with the second composition prior to administration of the insecticidal preparation, and an insect growth inhibiting effective amount of an insect growth regulator (IGR) component packaged with either the first or the second composition, wherein permethrin is present in about 45% to 65% by weight of the preparation.

2. The insecticidal preparation of claim 1, wherein the first insecticide composition is packaged in a first chamber, and the second insecticide composition is packaged in a second chamber, wherein the first chamber and the second chamber are packaged together but separated by at least one barrier which prevents interaction between the first and second insecticide compositions prior to administration of the insecticide preparation.

3. The insecticidal preparation of claim 2, wherein the first chamber and the second chamber are attached or encompassed by a container.

4. The insecticidal preparation of claim 1, wherein the IGR component comprises pyriproxyfen.

5. The insecticidal preparation of claim 4, wherein the preparation includes 5 to 15% by weight dinotefuran and 1 to 2% by weight pyriproxyfen.

6. The insecticidal preparation of claim 1, wherein the IGR component comprises methoprene.

7. The insecticidal preparation of claim 1, wherein the preparation further comprises an effective amount of triphenyl phosphate (TPP) to enhance the efficacy of the first or second insecticide composition.

8. The insecticidal preparation of claim 1, wherein the preparation is effective to achieve at least a 80% kill rate for fleas and at least a 80% kill rate for ticks.

9. The insecticidal preparation of claim 8, wherein the preparation is effective to achieve at least a 90% kill rate for fleas and at least a 90% kill rate for ticks.

10. The insecticidal preparation of claim 1, wherein the preparation is not irritating to dogs and is effective to kill ticks and fleas with applications of less than 10 ml to a dog.

11. The insecticidal preparation of claim 1 wherein one application of the preparation is effective to kill fleas and ticks for one month.

12. A method for controlling insect infestation in an animal, the method comprising applying the insecticidal preparation of claim 1 to the animal.

13. The method of claim 12, wherein the preparation is packaged in two separate containers.

14. The method of claim 12, wherein the preparation is packaged in one container encompassing the first and second chambers.

15. The method of claim 12, wherein the first and second compositions are encompassed by a container, wherein the container is a single dose package.

16. The method of claim 12 wherein the animal is a dog.

17. The method of claim 16 wherein the insect infestation comprises flea and tick infestation.

* * * * *